United States Patent [19]

Reese

[11] 4,449,929
[45] May 22, 1984

[54] DENTURE ALIGNMENT KIT

[75] Inventor: Russell I. Reese, Ontario, Calif.

[73] Assignee: Pfizer Inc., New York, N.Y.

[21] Appl. No.: 407,210

[22] Filed: Aug. 11, 1982

Related U.S. Application Data

[63] Continuation of Ser. No. 230,071, Jan. 30, 1981, abandoned.

[51] Int. Cl.³ .............................................. A61C 11/00
[52] U.S. Cl. ........................................ 433/56; 433/72; 433/75
[58] Field of Search ................... 433/56, 68, 72, 75; 33/174 D, 474, 476

[56] References Cited

U.S. PATENT DOCUMENTS

| | | | |
|---|---|---|---|
| 1,315,333 | 9/1919 | Roads | 33/476 |
| 1,470,530 | 10/1923 | Hohmann | 33/476 |
| 1,639,626 | 8/1927 | Badger | 433/56 |
| 2,138,254 | 11/1938 | Mink | 433/56 |
| 2,768,442 | 10/1956 | DeFurio | 433/56 |
| 3,439,421 | 4/1969 | Perkowski | 433/56 |

FOREIGN PATENT DOCUMENTS 1025564 3/1958 Fed. Rep. of Germany ........ 433/56

Primary Examiner—John J. Wilson
Attorney, Agent, or Firm—Charles J. Knuth; Peter C. Richardson; Harold W. Ordway

[57] ABSTRACT

A transparent occlusal guide and a wedge-shaped cusp ridge locator are used in transferring the crest line of the lower record base to establish a precise line for the setting of the lingual cusps of the upper posterior teeth during the setup stage of full denture fabrication.

1 Claim, 6 Drawing Figures

DENTURE ALIGNMENT KIT

This is a continuation of application Ser. No. 230,071 filed on Jan. 30, 1981, now abandoned.

BACKGROUND OF THE INVENTION

This invention concerns a means for establishing the proper positioning of particularly the upper and lower posterior teeth during the setup stage of full denture fabrication.

The fabrication of full dentures normally involves several stages or steps. In a typical denture preparation, the dentist initially makes impressions of the upper and lower gums of the edentulous mouth using such as dental alginate impression material. Master casts of standard quality dental stone are then formed from the hardened and dried impressions. Acrylic resin record bases are molded from the casts after the ridge areas on the casts are built up with baseplate wax. During the so-called setup stage, occlusion rims of baseplate wax are formed on the record bases, the patient's bite registration is verified, and the anterior and posterior artificial teeth are set into the record bases with the aid of an articulator. The resulting trial dentures are then checked for fit, and permanent dentures are fabricated from molds of the trial dentures.

The crest of the lower ridge of the edentulous mouth is recognized as an important factor influencing the positioning of all lower posterior denture teeth. Lower denture stability generally occurs when the lower posterior teeth are positioned with their centers directly above or slightly lingual of the crest of the ridge. In current practice, this positioning is primarily attempted using the eye and judgement of the denture fabricator. Such a technique requires the ability of a skilled technician, and even then is highly subject to human error.

It is therefore the primary objective of the present invention to provide a means employing the lower ridge crest line which can be used by even relatively unskilled technicians to easily and accurately position the posterior teeth during the setup stage of full denture fabrication.

SUMMARY OF THE INVENTION

Such means to facilitate accurate positioning of artificial teeth during the setup stage in the fabrication of full dentures is provided in the form of a kit, the kit comprising an occlusal guide and a cusp ridge locator.

The guide comprises a rigid transparent sheet having a rear edge for contacting the lower record base at the retromolar pads while the guide is positioned in the contemplated occlusal plane of the dentures. The locator comprises a rigid wedge-shaped sheet having adjacent first and second edges meeting at an acute angle, the first edge contacting the ridge crest of the lower record base when the locator is wedged between the guide and the lower record base in a position substantially normal to the guide with the second edge resting against the lower surface of the guide, the locator having inscribed on a surface thereof a series of parallel lines normal to the second edge, whereby the contact point of the first edge with the ridge crest may be visually projected onto the transparent guide and marked on the upper surface thereof. A progression of the projected contact points thus constitutes transfer of the crest line of the lower ridge crest to the upper guide surface, the transferred line establishing the cusp ridge line in the occlusal plane to which the occlusal surfaces of the posterior maxillary and mandibular teeth are set as they are attached to their respective record bases.

Preferably, the rear edge of the guide defines the two equal sides of an isoceles triangle having an obtuse apex angle and is beveled downward; the remaining edge of the guide defines a circular arc; and the locator defines a right triangle and is transparent.

BRIEF DESCRIPTION OF THE DRAWINGS

The above and other objects, features and advantages of the present invention will be apparent from the following detailed description of an embodiment thereof in conjunction with the accompanying drawings wherein like reference numerals indicate like structures throughout the several views.

DESCRIPTION OF THE PREFERRED EMBODIMENTS

Figure 1:
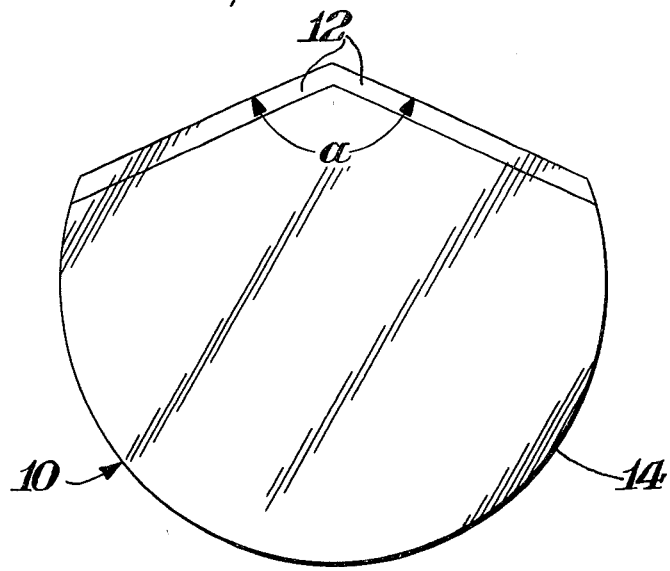
FIG. 1 is a top plan view of the occlusal guide of the present invention.
Figure 2:
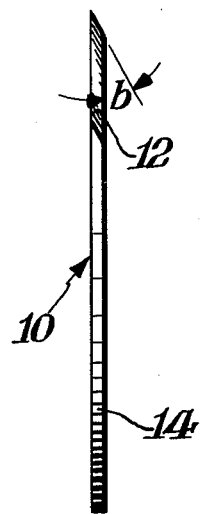
FIG. 2 is a side elevational view of the occlusal guide.
Figure 3:
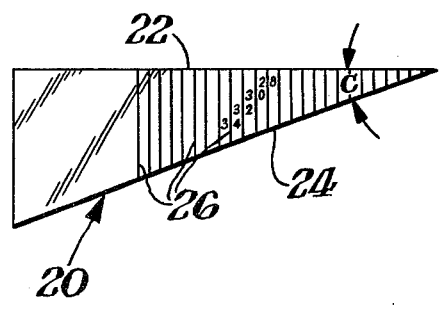
FIG. 3 is a front elevational view of the cusp ridge locator of the present invention.

The individual components of the denture alignment kit of the present invention are depicted in FIGS. 1 thru 3.

The occlusal guide 10, as shown in FIGS. 1 and 2, comprises a rigid transparent sheet, for example of polyacrylate resin, suitably having a thickness of about 2 mm. The rear edge 12 of guide 10 defines the two equal sides of an isoceles triangle having an obtuse apex angle "a" of about 135 degrees, each of the sides appropriately having a length of about 4.5 cm. The rear edge 12 is beveled downward and inward from the top surface, as shown in FIG. 2, for example at an angle "b" of about 30 degrees. The remaining edge 14 of guide 10 defines an arc of a circle preferably having a radius of about 4.5 cm.

The cusp ridge locator 20, as shown in FIG. 3, comprises a rigid sheet which may also be of transparent polyacrylate resin having a thickness of about 2 mm. The locator 20 defines a right triangle in which, for example, one side 22 having a length of about 7 cm meets the hypotenuse 24 at an acute angle "c" of about 20 degrees. The locator 20 has inscribed on one surface thereof a series of parallel lines 26 which start at the apex of angle "c", are normal to side 22 and are regularly spaced, preferably at about 2 mm intervals. The lines 26 which are numbered 28 thru 34 are identified as such to assist in posterior tooth selection.

Figure 4:
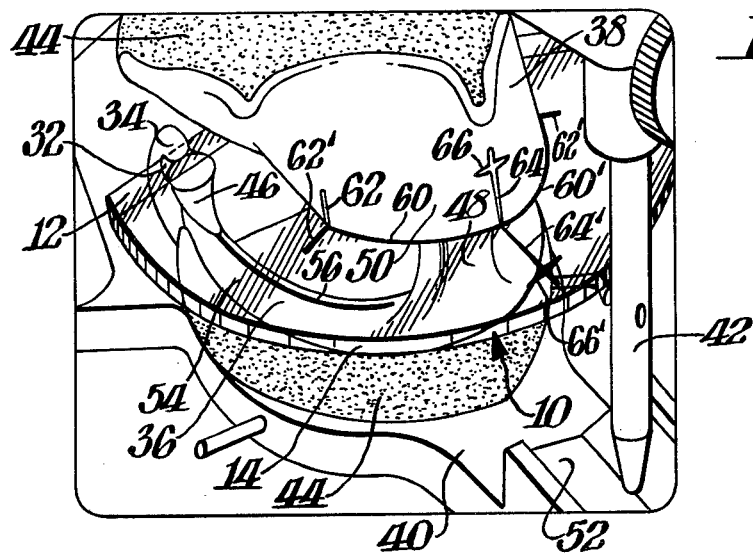
FIG. 4 is a pictorial view showing the occlusal guide positioned in the contemplated occlusal plane of the dentures being fabricated.
Figure 5:
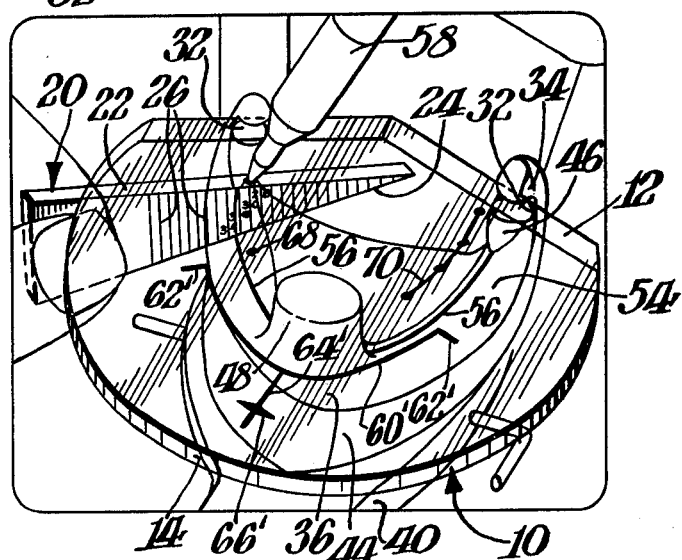
FIG. 5 is a second pictorial view showing use of the occlusal guide and cusp ridge locator in the transfer of the lower ridge crest line.
Figure 6:
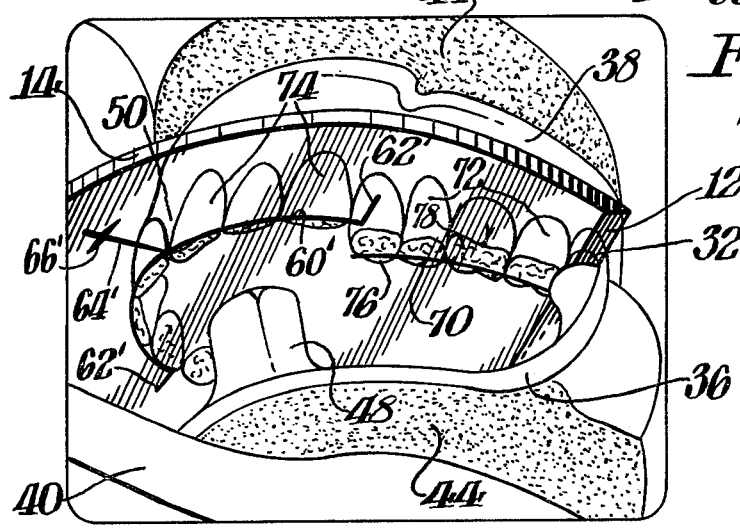
FIG. 6 is a third pictorial view showing the placement of the upper posterior teeth along the transferred crest line.

FIGS. 4 thru 6 depict certain aspects of the setup stage during the fabrication of full dentures, indicating how the guide 10 and locator 20 are used to accurately position the false teeth.

FIG. 4 depicts the final condition in the establishment of the working occlusal plane. The rear edge 12 of guide 10 has been inserted into orientation grooves 32 located at the two-thirds level of the retromolar pads 34 of lower, or mandibular, record base 36, orientation grooves 32 being established as explained hereinafter. Both lower record base 36 and upper, or maxillary, record base 38 are mounted to a standard articulator 40 with an incisal guide pin 42, the record bases 36,38 being adapted to the articulator 40 with dental plaster 44. Guide 10 is supported posteriorly by posterior wax supports 46 just anterior of each orientation groove 32, and anteriorly by anterior wax post 48. The working occlusal plane is established when only the most anterior position of occlusal rim 50 of upper record base 38 just touches the upper surface of guide 10 as incisal guide pin 42 just touches guide table 52.

Following is a brief description of the denture fabrication to this point.

Impressions of the upper and lower gums of an edentulous mouth are taken using such as dental alginate impression material. The impressions are allowed to harden and are then rinsed with water and dried. Master casts are made from the impressions using standard dental stone for processing record bases. The upper cast is post dammed in the usual manner and a softened sheet of baseplate wax is adapted to only the ridge. A flexible anatomical pattern is adapted to the palatal portion of the upper cast using a thin wax wash, and all boundaries then are sealed with utility wax. The retromolar pads are outlined on the lower cast, and the two-thirds height from the base of each pad is transferred to the adjacent land area. Softened baseplate wax is adapted over the lower cast ridge, care being exercised to create and preserve in the wax the crest of the ridge, and all borders are then sealed with utility wax. The wax over the retromolar pads is softened and the rear edge 12 of the occlusal guide 10 is pressed into the wax at the two-thirds elevation of the pads while viewed antero-posteriorly to create the orientation, grooves 32 of the processed lower record base 36.

The wax patterns are flasked using reversible hydrocolloid, and the upper and lower stabilized record bases 38,36 are fabricated following the standard procedure for processing fluid resin dentures. The record bases 38,36 are recovered, the master casts destroyed, and wax occlusion rims are adapted to the bases. The record bases 38,36 are then inserted into the edentulous mouth, the various intra-oral conditions are confirmed and proper bite is established using softened check-bite wax. When the bit wax has hardened, the record bases 38,36 are secured to a standard articulator 40 using dental plaster 44 with moist pumice to fill the undercuts, and the incisal guide pin 42 of the articulator 40 is adjusted to just touch the guide table 52.

The articulator 40 is opened, the bite wax is removed, all wax is stripped from the lower record base 36, and the crest of lower ridge 54 is marked as a continuous line 56 from the left to right orientation grooves 32 using a pen 58, shown in FIG. 5, which contains water-insoluble black ink. Posterior wax supports 46 and an anterior wax post 48 are attached, the occlusal guide 10 is inserted in the orientation grooves 32, and the working occlusal plane is established as indicated hereinbefore. All records, including the esthetic contour line 60, distal of cuspid lines 62, mid-line 64 and high lip line 66 are transferred from the occlusion rim 50 of the upper record base 38 to the upper surface of guide 10, the transferred lines being 60', 62', 64' and 66', respectively.

FIG. 5 depicts the transfer of the ridge crest line 56 of lower record base 36 to the upper surface of occlusal guide 10. The cusp ridge locator 20 is wedged into position between the guide 10 and the lower record base 36, the hypotenuse 24 of locator 20 contacting the crest of lower ridge 54 of lower record base 36 in a position substantially normal to guide 10 with side 22 of locator 20 resting against the lower surface of guide 10, while proximate to transferred distal of cuspid line 62'. Using parallel lines 26, the point of contact of locator 20 with ridge crest line 56 is transferred to the upper surface of guide 10 by placing a black dot 68 from pen 58 on the surface directly above the point of contact. This process is repeated, for example at about 7 mm intervals, along each ridge crest line 56 until 4 or 5 dots have been transferred. Generally the most anterior dot is placed directly above ridge crest line 56 and each dot 68 thereafter is positioned 1 mm lingual of the preceding dot 68. The several dots 68 on each side are connected, using pen 58, to form right and left cusp ridge lines 70 to guide the positioning of all upper posterior teeth 72.

This positioning is depicted in FIG. 6. Initially, the upper anterior teeth 74 are positioned, one at a time, lingual to transferred esthetic contour line 60' beginning with the central incisor. The central incisors are set against guide 10, while the lateral incisors are set 1 mm and the cuspids 0.5 mm above guide 10. The upper bicuspids or posterior teeth 72 are then positioned, starting with the first bicuspid, with the lingual cusps 76 centered on the cusp ridge line 70 and the occlusal surface 78 in contact with guide 10. The transparency of guide 10 provides accurate visual perception for the positioning of all upper teeth.

To complete the denture fabrication, guide 10, posterior wax supports 46 and anterior wax post 48 are removed, and the lower teeth are positioned in their appropriate relationship to the upper arrangement, the voids in the setup wax being filled to provide an even surface. Labial patterns are then adapted to the upper and lower base setups. Following confirmation of the trial dentures in the edentulous mouth, molds are made of the trial dentures and the final dentures are processed.

While the invention has been described in connection with a preferred embodiment, it also includes alternatives, modifications and equivalents within the spirit and scope of the appended claims.

I claim:

1. A method of facilitating the accurate positioning of artificial teeth during the setup stage in the fabrication of full dentures, which comprises the steps of contacting a lower record base with an occlusal guide comprising a rigid transparent sheet with a rear edge, said contact being between said rear edge and the retromolar pads of said base, while said guide is positioned in the contemplated occlusal plane of said dentures, contacting a cusp ridge locator comprising a rigid wedge-shaped sheet having adjacent first and second edges meeting at an acute angle at said first edge with the ridge crest of said lower record base, said locator being wedged between said guide and said lower record base in a position substantially normal to said guide with said second edge of said locator resting against the lower surface of said guide, and visually projecting the contact point of said first edge with said ridge crest onto said guide with the aid of one of a series of parallel lines inscribed on a surface of said locator normal to said second edge and extending from said second to said first edge, and marking said projection on the upper surface thereof, repeating said contacting and projecting steps to establish a progression of said projected contact points constituting transfer of the crest line of said lower ridge crest to said upper guide surface.

* * * * *